ns Patent [19]

United States Patent [19]

Schwan

[11] 4,228,303
[45] Oct. 14, 1980

[54] 3-(3,4-DIHYDROXYPHENYL)-N-(4-NITROBENZYL)ALANINE HYDROBROMIDE

[75] Inventor: Thomas J. Schwan, Norwich, N.Y.

[73] Assignee: Morton-Norwich Products, Inc., Norwich, N.Y.

[21] Appl. No.: 51,512

[22] Filed: Jun. 25, 1979

[51] Int. Cl.³ .............................................. C07C 79/46
[52] U.S. Cl. .................................... 562/435; 424/319; 560/21
[58] Field of Search ....................... 562/433, 446, 435; 424/319, 309; 560/38, 40, 39, 21

[56] References Cited

U.S. PATENT DOCUMENTS

| 3,852,338 | 12/1974 | Kaiser et al. | 560/29 |
| 3,859,331 | 1/1975 | Kaiser et al. | 562/446 |
| 4,020,060 | 4/1977 | Erickson et al. | 562/446 |
| 4,058,642 | 11/1977 | Renth et al. | 560/40 |

OTHER PUBLICATIONS

Tanabe, Chem. Abst., vol. 60, #2770g, (1967).

*Primary Examiner*—Joseph E. Evans
*Assistant Examiner*—James H. Reamer
*Attorney, Agent, or Firm*—Anthony J. Franze

[57] ABSTRACT

The compound of the formula:

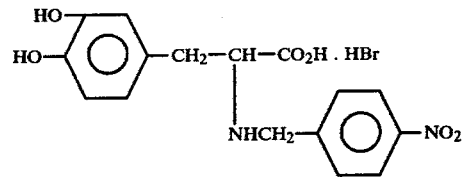

is active as an antibacterial agent.

1 Claim, No Drawings

3-(3,4-DIHYDROXYPHENYL)-N-(4-NITROBENZYL)ALANINE HYDROBROMIDE

This invention is concerned with chemical compounds. In particular, it is concerned with the compound of the formula:

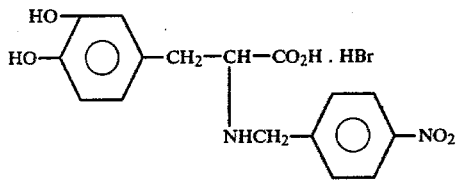

This compound is useful as a urinary tract antibacterial agent. When orally administered to rats at 100 mg/kg, the collected urine therefrom inhibited the growth of *Proteus mirabilis* and Staphylococus aureus.

In order that this invention may be readily available to and understood by those skilled in the art, the following examples are included:

A. Ethyl 3-(3,4-Dimethoxyphenyl)alaninate

A 47 g (0.21 mole) portion of 3,4-dimethoxyphenylalanine in 450 ml of absolute ethanol was treated with 31 ml of concentrated $H_2SO_4$. The reaction mixture was refluxed for 5 hours and poured into 1.6 l. of $H_2O$. The solution was basified with a solution of 61 g of $K_2CO_3$ in 200 ml of water. The basified solution was extracted with three 600 ml portions of ethyl acetate. The combined extracts were washed with 1.4 l. of water, dried over $MgSO_4$ overnight and filtered. The filtrate was concentrated under reduced pressure to give 27 g (51%) of the desired product, a light yellow-brown viscous oil which crystallized upon refrigeration.

B. Ethyl 3-(3,4-Dimethoxyphenyl)-N-(p-nitrobenzyl)alaninate Hydrochloride

A 22 g (0.087 mole) portion of A, 18.7 g (0.087 mole) of p-nitrobenzylbromide, 11.9 g (0.087 mole) of $K_2CO_3$ and 200 ml of absolute ethanol were placed in a 1 l. 3-neck flask and refluxed with stirring for 5 hours. The slurry was diluted with 375 ml of $H_2O$ and extracted with three 150 ml portions of ethyl acetate. The extracts were washed with 150 ml of $H_2O$, dried over $MgSO_4$ overnight, filtered and concentrated to dryness to give a yellow-brown semi-solid.

The residue was taken up in 75 ml of ethanol. Methanolic HCl (100 ml) was added and the solution was concentrated to dryness. The residue was taken up in 80 ml of ethanol and 25 ml of benzene and the solution again concentrated to dryness under reduced pressure. The resulting crude hydrochloride was taken up in 94 ml of boiling acetonitrile and filtered. The filtrate was diluted with 470 ml of toluene, refrigerated overnight and filtered. The resulting yellow solid was washed with 25 ml of a 5:1 toluene-acetonitrile and air dried, m.p. 163°–166°; yield 27 g (73%).

C. 3-(3,4-Dihydroxyphenyl)-N-(4-nitrobenzyl)alanine hydrobromide

A 21.0 g (0.049 mole) portion of B in 210 ml of 48% HBr was refluxed for 2.5 hours. The excess 48% HBr was removed under reduced pressure. The residue was dissolved in 150 ml of ethanol; 45 ml of benzene was added and the solvents were removed under reduced pressure leaving a yellow-green residue. This residue was dissolved in 200 ml of boiling acetonitrile and filtered, leaving less than 1 g of a light green residue. The filtrate was refrigerated overnight and filtered. The light yellow solid was washed with 20 ml of acetonitrile and air dried, m.p. 227°–229° dec.; yield: 5.8 (29%).

An analytical sample, m.p. 224°–226° dec., was obtained by drying at 160° in vacuo.

Anal. Calcd. for $C_{16}H_{16}N_2O_6 \cdot HBr$: C, 46.50; H, 4.41; N, 6.41. Found: C, 45.94; H, 4.43; N, 6.45.

What is claimed is:

1. The compound 3-(3,4-dihydroxyphenyl)-N-(4-nitrobenzyl)alanine hydrobromide.